United States Patent [19]

Nahle

[11] 4,082,842
[45] Apr. 4, 1978

[54] MEDICANT COMPOSITION FOR THE TREATMENT OF DIABETES

[76] Inventor: Armando Nahle, 828 Richard Dr., El Paso, Tex. 79907

[21] Appl. No.: 551,992

[22] Filed: Feb. 21, 1975

[51] Int. Cl.² ............... A61K 31/635; A61K 31/375; A61K 31/18

[52] U.S. Cl. .................................... 424/229; 424/280; 424/321

[58] Field of Search .................. 424/229, 321, 280

[56] References Cited

U.S. PATENT DOCUMENTS 3,298,917  1/1967  Bicking .............................. 424/321

OTHER PUBLICATIONS

Heerd et al – Chem. Abst. vol. 70 (1969) 87843u.

Zymaris – Chem. Abst. vol. 65 (1966) p. 9415f.

*Primary Examiner*—Sam Rosen
*Attorney, Agent, or Firm*—James J. Brown

[57] ABSTRACT

An orally administered medicant composition useful for the treatment of diabetes mellitus; whose constituents are a hypoglycemic of the sulphonylurea derivative type together with an anti-bacterial sulfonamide and ascorbic acid. A unit dosage of one preferred formulation is comprised of 0.5 gram tolbutamide, 100 milligrams sulfamethox-pyridazine and 50 milligrams ascorbic acid. A typical treatment that has proven successful in correcting numerous diabetic conditions may begin with as many as six unit dosages the first day, thereafter the dosage is reduced, then sustained at a level in accordance to the response of the patient; treatment is terminated usually after a six month period.

5 Claims, No Drawings

MEDICANT COMPOSITION FOR THE TREATMENT OF DIABETES

BACKGROUND OF THE INVENTION

The present invention relates to medicants useful for the treatment of diabetes and more particularly concerns an orally administered medicant composition useful for the treatment of diabetes mellitus.

A number of cases of diabetes are of a mild nature; sometimes falling into this classification is diabetes that makes itself manifest during or following an illness or diabetes that develops in the obese, mature individual. This milder diabetes often responds very favorably to treatment and/or diet to the extent that the diabetic symptoms disappear and the individual may be considered cured. Other than these marginal or latent cases, diabetes is characterized as a disease that may be controlled but not cured.

To date, the exact cause or the exact body system malfunction leading to a diabetic condition is not known. Nevertheless, treatment of this once dread disease is now very successful. The breakthrough came with the discovery of insulin; then came the oral medicaments which for many diabetics meant release from the daily insulin injections. But the success of treatment represents a life-long commitment to a regimen of insulin injections or oral medicaments in conjunction with a controlled diet for neither the insulin nor the oral medicaments effect a cure, rather the two serve to control the disease.

If a predisposing factor for diabetes is to be picked, it would likely be an infectious disease since the symptoms of diabetes have developed more often during or following such a disease than with other types. It has been reported that studies at the Children's Medical Research Foundation in Sydney, Australia implicate congenital rubella as the infectious disease most likely to be the cause of diabetes.

A hypothesis that was followed in developing the medicant composition of this invention for diabetes is in line with an infectious disease cause: While the sulfonylurea type hypoglycemic acts to stimulate insulin production (or its effectiveness), the sulfonamide acts to overcome any active or latent infection that has affected the body's insulin production or utilization system; meanwhile, the ascorbic acid promotes a general enhancement of the organic defenses of the body. These three actions in combination correct deficiencies of the body's insulin system.

It is a first object of this invention to provide an orally administered medicant composition useful for the treatment of diabetes mellitus.

Another object of this invention is to provide such an oral medicant composition for the treatment of diabetes mellitus comprising as the active ingredients a hypoglycemic of the sulphonylurea derivative type, an anti-bacterial sulfonamide and ascorbic acid.

Yet another object of this invention is to provide an oral medicant composition for the treatment of diabetes mellitus comprising as the active ingredients specifically effective amounts of tolbutamide, sulfamethoxypyridazine and ascorbic acid.

A still further object of this invention is to provide such an oral medicant composition for the treatment of diabetes mellitus with whose treatment is required only a casual diet observance.

SUMMARY OF THE INVENTION

The present invention is directed to an orally administered medicant composition comprised of 65 to 85 weight percent, preferably 70 to 80 weight percent, of a hypoglycemic of the sulphonylurea derivative type; 10 to 30 weight percent, preferably 10 to 20 weight percent, of an anti-bacterial sulfonamide and 5 to 10 weight percent ascorbic acid. A unit dosage of one preferred formulation consists of about 77 weight percent tolbutamide, about 15.3 weight percent sulfamethoxpyridazine and 7.7 weight percent ascorbic acid. The dosage for treating diabetes mellitus is 3 to 6 units the first day, 3 to 4 units the second day, and 1 to 3 units thereafter usually for a period of six months. Within the ranges stated, the exact dosage is determined initially on the basis of the severity of the diabetic condition, then on the basis of the response to the treatment. The period of treatment typically extends over six months. The medicant of this invention requires that there be some production of insulin in the body since it is not a substitute for insulin. Diabetics in an acidosis or coma condition should be treated with presently established procedures but, because of the excellent results experienced with the medicant of this invention, it should certainly be prescribed under medical surveillance, once control over the acidosis or coma condition has been gained. The medicant of this invention should not be prescribed for diabetic children except under strict medical surveillance. Generally, precautions to be considered are in line with those of tolbutamide and sulfamethox-pyridazine.

DESCRIPTION OF ONE PREFERRED EMBODIMENT

An oral medicant composition useful for the treatment of diabetes mellitus is a hypoglycemic of the sulphonylurea derivative type, an anti-bacterial sulfonamide and ascorbic acid. A unit dosage of one preferred formulation is comprised of 0.5 gram tolbutamide, 100 milligrams sulfamethoxpyridazine and 50 milligrams ascorbic acid. This proportion of the active ingredients was established to provide flexibility to meet the varying requirements of individual patients, yet to be in keeping with existing recommended dosages of the individual medicant ingredients.

Thus, a single unit of the preferred oral medicant of the present invention contains a total of 650 milligrams of composition and the daily unit dosage of 1–6 units corresponds to 650–3900 milligrams of total composition. Following the preferred, extended dosage, 3–6 units or 1950–3900 milligrams are administered the first day, 3–4 units or 1950–2600 milligrams the second day, and 1–3 units or 650–1950 milligrams the third day.

When the prescription for the medicant of this invention is one unit per day, it should be taken after breakfast; when taking more than one unit a day, the dosage can be distributed to be taken after meals of the day.

The composition of this invention may be formulated into various pharmaceutical forms, e.g., capsules or tablets together with any suitable fillers or binders.

Treatment of diabetes with the composition of this invention begins with a dosage of from three to six units the first day, three to four units the second day, and one to three units thereafter with the exact dosage within the ranges adjusted to each individual patient and his response to treatment. The treatment period is typically six months.

The composition of this invention can be expected to be effective with a substantially larger number of diabetic patients as compared to the patients with which presently available oral medicants are effective.

For those patients on insulin that may respond to treatment with the composition of this invention, the insulin prescription is reduced in steps at the same time that the medicant of this invention is increased. Bearing in mind that there cannot be a fixed prescription for all patients, a schedule of treatment that has proven successful in transferring a patient from insulin to the medicant of this invention is illustrated with an example of a patient taking 40 units of insulin a day. With close medical surveillance, for 15 days the insulin is reduced to 30 units while 2 units of the medicant of this invention is prescribed. Subsequently in thirty day periods the insulin is reduced to 20, 10 and 5 units while for the corresponding periods the dosage of the medicant of this invention is 3, 4 and 5 units. The insulin is then stopped altogether and the dosage of the medicant of this invention is adjusted to the response of the patient and continued usually for a period of three months. If ketone bodies should appear in the urine at any time, an instant switch to full insulin treatment should be made.

The medicant of this invention is not a substitute for insulin; there must be some insulin activity in the diabetic patient if the medicant is to successful. Any patient in an acidosis or coma condition should be treated with presently established procedures. After control over these emergency conditions is gained, treatment with the medicant of this invention should be considered along the lines described in the preceding paragraph.

Precautions to be observed in prescribing the medicant of this invention are those of the sulphonylurea derivatives and the sulfonamides and in the one preferred embodiment described, the precautions to be observed are those associated with tolbutamide and sulfamethox-pyridazine. The medicant of this invention should be prescribed for children only under strict medical surveillance. For children and for those persons sensitive to the sulfamethox-pyridazine, the amount of this ingredient in the unit dosage of the one preferred formulation described may be reduced from 100 to 50 milligrams. The usual period of treatment of six months may then likely require being extended an additional two to three months. Neither strict diets nor weight control measures are required in conjunction with treatment with the composition of this invention. When treatment is begun, the patient should exclude sweets and refined flour foods, particularly the pastas (spaghetti, macaroni, etc.). After a three month period, small amounts of the pasta foods may be taken. After the treatment period is terminated, all foods may be taken but the individual should be made aware of diet and weight control consistent with general well-being.

A high rate of success has been experienced with the subject medicant in treating diabetic patients to the point that all medication is discontinued. Data transcribed from actual clinical records of five diabetics is presented below to show typical progress of patients treated with the composition of this invention. The blood sugar of glucose level entries are in reference to a normal range of from 65 to 100 milligrams glucose per 100 milli-liters of blood.

| Case No. | Glucose Medicant Time | Glucose Medicant Time | Glucose Medicant Time | Glucose Medicant Time | Glucose Medicant Time |
|---|---|---|---|---|---|
| A | 188 2 units (1st day) | 109 1 unit (26th day) | 93.5 1 unit (1 month) | | |
| B | 114 2 units (1st day) | 274* 2 units (23rd day) | 130 2 units (50th day) | 180 2 units (71st day) | 156 2 units (114th day) |
| | 105 1 unit (154th day) | 119 (184th d.) | 104** (240th d.) | 105 (302nd day) | 71.5 (2yr.7mo., 8 days) |

*Switch from insulin to medicant of this invention begun.
**Treatment stopped at this time. Patient has not received any medicant for diabetes since.

| | | | | | |
|---|---|---|---|---|---|
| C | 211* 2 units (1st day) | 150 2 units (30 days) | 116** 2 units (40 days) | | |

*Patient did not perservere in adhering to medical supervision; in poor control, yet taking 30 units insulin. Switch to medicant of this invention begun after 211 glucose analysis made.
**Insulin stopped; patient receiving only medicant of this invention.

| | | | | | |
|---|---|---|---|---|---|
| D | 138* 2 units (1st day) | 212 2 units (49th day) | 130 1 unit (91st day) | 133 1 unit (126th day) | 128 1 unit (168th day) |
| | 127** 1 unit (224th day) | 114 1 unit (268th day) | 104 1 unit (297th day) | | |

*Individual drinks. In poor control for several years with presently available orals. Was switched to medicant of this invention.
**Treatment with medicant of this invention discontinued after this analysis. No other medication for diabetes taken. Patient has not altered drinking pattern.

| | | | | | |
|---|---|---|---|---|---|
| E | 282* (1st day) | 251.25** 2 units (246th day) | Neg.. 1 unit (324th day) | 127.5*** 1 unit (444th day) | |

*Analysis while under care of different doctor; patient possibly not following prescription.
**Treatment with medicant of this invention begun.
***Still receiving medicant of this invention.

The foregoing description is to be clearly understood as given by way of illustration and example only, modifications and variations may be made without departing from the spirit and scope of the present invention.

I claim:

1. A composition effective for treating diabetes mellitus when administered in daily dosages of about 650 to 3900 milligrams, said composition comprising 65 to 85 weight percent of a hypoglycemic of the sulfonylurea type, 10 to 30 weight percent of sulfamethoxypyridazine, and 5 to 10 weight percent ascorbic acid.

2. The composition of claim 1 which contains 70 to 80 weight percent of said hypoglycemic and 10 to 20 weight percent of said sulfomethoxypridazine.

3. The composition of claim 1 wherein said hypoglycemic is tolbutamide.

4. A method of treating diabetes mellitus which comprises administering daily dosages of about 650–3900 milligrams of a composition comprising 65 to 85 weight percent of a hypoglycemic of the sulfonylurea type, 10 to 20 weight percent of sulfamethoxypyridazine and 5 to 10 weight percent ascorbic acid.

5. The method of claim 4 which comprises administering about 1950–3900 milligrams of said composition the first day of treatment, 1950–2600 milligrams the second day, and 650–1950 hereafter.

* * * * *